United States Patent [19]

Fryar et al.

[11] 4,393,643

[45] Jul. 19, 1983

[54] PROCESS FOR FORMING A BARRIER PHASE

[75] Inventors: Durward Fryar, Burlington, Ky.; Jerome J. Schmitz, Cincinnati, Ohio

[73] Assignee: The Procter & Gamble Company, Cincinnati, Ohio

[21] Appl. No.: 402,870

[22] Filed: Jul. 29, 1982

Related U.S. Application Data

[63] Continuation-in-part of Ser. No. 306,808, Sep. 29, 1981, abandoned.

[51] Int. Cl.³ .......................... B29D 3/00; B65B 7/28
[52] U.S. Cl. ...................................... 53/471; 53/452; 53/467; 53/474; 53/476; 264/255; 264/262; 264/267; 264/304; 264/334
[58] Field of Search ............... 264/255, 267, 261, 262, 264/334, 304, 305; 53/409, 452, 471, 474, 476, 467

[56] References Cited

U.S. PATENT DOCUMENTS

| | | | |
|---|---|---|---|
| 1,917,483 | 7/1933 | Arimoto | 53/440 |
| 1,919,692 | 7/1933 | Falkendorf | 53/440 |
| 1,987,084 | 1/1935 | Snodgrass | 53/440 |
| 2,299,039 | 1/1935 | Scherer | 264/301 |
| 3,279,999 | 10/1966 | Harrison et al. | |
| 3,315,344 | 4/1967 | Niclas | |
| 3,462,524 | 8/1969 | Lemelson | |
| 3,794,453 | 2/1974 | Padilla et al. | 264/301 |
| 3,961,089 | 6/1976 | Dogliotte | |
| 4,054,636 | 10/1977 | Menig | |
| 4,076,788 | 2/1978 | Ditto | |
| 4,147,750 | 4/1979 | Gerea et al. | |
| 4,172,113 | 10/1979 | Featherstone et al. | |
| 4,202,879 | 5/1980 | Shelton | |
| 4,222,973 | 9/1980 | Kasper | |

Primary Examiner—Willard E. Hoag
Attorney, Agent, or Firm—Douglas C. Mohl; Richard C. Witte; John V. Gorman

[57] ABSTRACT

A process for forming a barrier phase between two incompatible phases comprising forming a thin layer of barrier material on the outer surface of a pin; placing the coated pin into a package or mold form designed to contain the total product; putting the molten outer phase into the space between the coated pin and the outer wall(s) of the package or mold form and allowing the outer phase to solidify; removing the pin leaving the barrier phase attached to the outer phase; and putting the inner phase into the space previously occupied by the pin.

10 Claims, 7 Drawing Figures

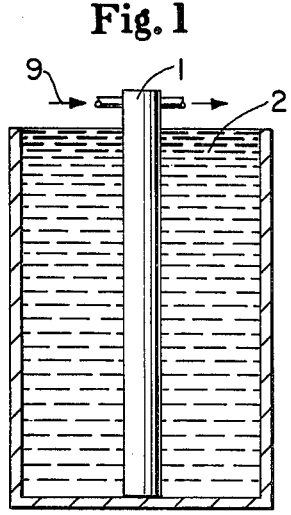
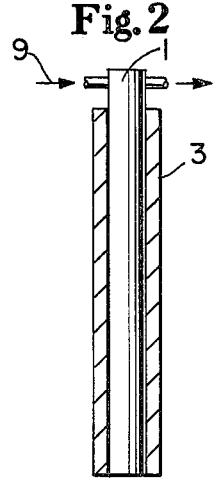
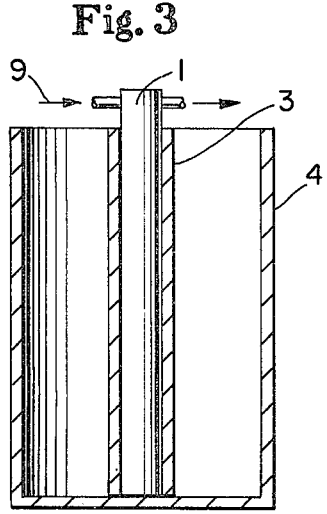
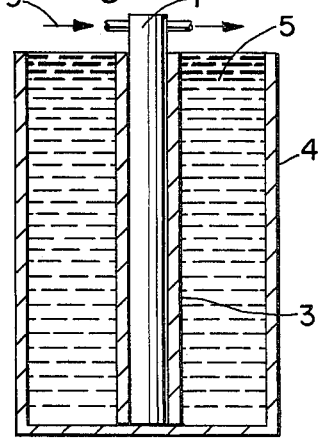
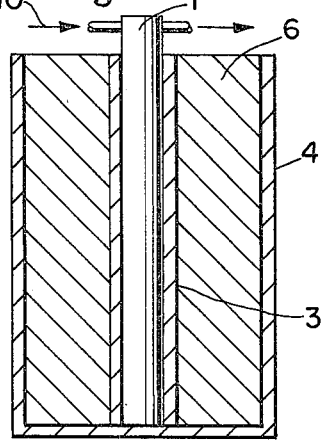
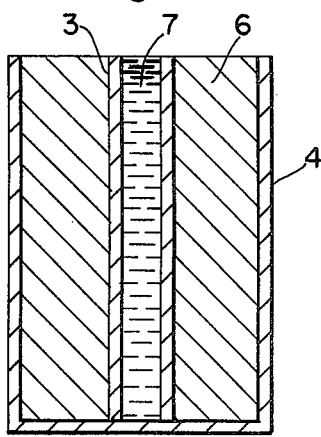
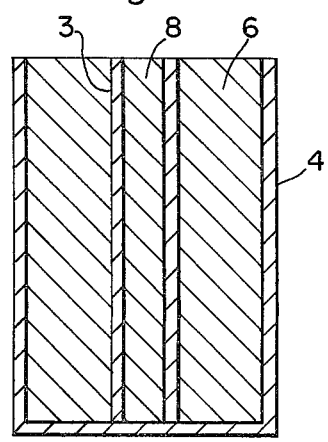

PROCESS FOR FORMING A BARRIER PHASE

RELATED APPLICATION

This is a continuation-in-part application of Ser. No. 306,808, filed Sept. 29, 1981 now abandoned.

TECHNICAL FIELD

The present invention relates to a process for forming a barrier phase between two incompatible phases in a product such as a cosmetic stick.

BACKGROUND OF THE INVENTION

Cosmetic sticks are well known for use in delivering a number of different agents to the skin. Such sticks are often constructed of wax-type materials or gelling agents such as soaps. The desire to get the best of both types of products has led to a variety of product executions.

Among the product executions which have been developed are deodorant and antiperspirant sticks. Included are deodorant and antiperspirant sticks which deliver active ingredients to the skin via a vehicle which glides easily over the skin surface and which imparts a cooling sensation to the skin both during and after application. Soap/alcohol gels can provide such cosmetic benefits. However, incorporation of conventional astringent antiperspirant salts into such gels tends to interfere with the gel structure and render it less cosmetically desirable. To solve such compatibility problems, soap/alcohol gel sticks have been formulated using special additives such as lactate salts. (See, for example, Teller; U.S. Pat. No. 2,732,327, issued Jan. 24, 1956 and Slater; U.S. Pat. No. 2,900,306, issued Aug. 18, 1959). Some soap/alcohol gel antiperspirant sticks have also been formulated in two phases with an inner core containing gel-compatible antiperspirant salts and an outer shell containing deodorant materials (See Bell, U.S. Pat. No. 2,970,083, issued Jan. 31, 1961).

Combination of a conventional waxy antiperspirant composition with a soap/alcohol gel to form a two-phase stick composition could enhance composition efficacy and improve composition cosmetic benefits. Such combination is, however, not made without certain difficulties. While each phase alone of such a stick composition is stable, contact between the two phases can cause destructive interaction between the two phases. The alcohol/gel phase experiences syneresis which is a bleeding or leading of the gelled alcohol from the gel structure or matrix. Such leaked alcohol can interact with components of the waxy phase and can thus consume or physically separate the phases, thereby resulting in an unacceptable consumer product.

These problems led to the development described in U.S. Pat. No. 4,202,879, May 13, 1980 to Shelton. Shelton's invention relates to the use of a thin waxy barrier between the phases. The method of applying the barrier, which is described at lines 35-50 of Column 15 in the patent, involves dipping the solidified inner phase of the stick into a bath containing the molten barrier mixture, removing the coated inner phase from the bath, letting the barrier solidify, placing the solidified barrier coated inner phase into a mold and adding the molten outer phase into the space between the coated inner phase and the wall of the mold. This approach, while providing a barrier phase, has been found to be not entirely satisfactory. Difficulties were encountered in handling the coated inner phase and in making the total product quickly.

In view of the aforementioned problems, there is the need for improved processes for placing a barrier between two incompatible phases. It is, therefore, an object of the present invention to provide an improved process for providing such barriers.

It is a further object of the present invention to provide a process for providing multi-phase antiperspirant sticks.

It is a further object of the present invention to provide such antiperspirant sticks in a fast and economical manner.

It has been surprisingly discovered that these objectives, which will become apparent from the following detailed disclosure, can be realized by coating a pin and then releasing the coating to the outer phase.

All percentages herein are by weight unless otherwise specified.

SUMMARY OF THE INVENTION

The present invention relates to a process for forming a barrier phase between two incompatible phases comprising forming a thin layer of barrier material on the outer surface of a pin; placing the coated pin into a package or mold form designed to contain the total product; putting the molten outer phase into the package or mold form and allowing the outer phase to solidify; removing the pin leaving the barrier phase attached to the outer phase; and putting the inner phase into the space previously occupied by the pin.

BRIEF DESCRIPTION OF THE DRAWINGS

All figures provide schematic cross sectional views.

FIG. 1 shows the pin, 1, immersed in a molten bath of barrier phase material, 2. A cooling medium, 9, circulates within the pin.

FIG. 2 shows the pin with a solid coating, 3, of barrier phase material.

FIG. 3 shows the coated pin in a container, 4, suitable for holding the entire product.

FIG. 4 shows the molten outer phase material, 5, in the container with the coated pin.

FIG. 5 shows the solid outer phase, 6, in the container with the coated pin. A heating medium, 10, circulates within the pin.

FIG. 6 shows the container with the pin removed and the barrier phase left attached to the solid outer phase. The molten inner phase, 7, is in the space previously occupied by the pin.

FIG. 7 shows the inner phase in a solified state, 8.

DETAILED DESCRIPTION OF THE INVENTION

The process of the present invention involves a number of steps which are described below.

Forming the Barrier

A hollow pin of appropriate size and optionally having a cooling medium circulating within is dipped into a container of molten barrier phase material. The pin is then removed from the barrier bath with a coating of barrier material on the pin's exterior wall(s). Depending on the particular composition of the barrier the temperatures required to keep it in a molten state and to deposit it on the pin may vary greatly. The temperature of the surface of the pin, obviously, must be kept below the solidification temperature of the barrier phase.

The preferred products of the present invention are cosmetic sticks such as antiperspirant sticks of the type described in the aforementioned Shelton patent.

In Shelton's compositions, the barrier phase serves to segregate the gel phase from the antiperspirant phase and thereby effectively eliminates the problem of destructive interfacial interaction. The barrier phase comprises from about 1% to 10%, preferably about 2% to 4% by weight of the total antiperspirant stick compositions. To insure that the barrier phase constitutes a continuous layer of protection, the barrier phase should have a minimum thickness of at least about 0.005 of an inch. Preferably, the barrier phase ranges in thickness from about 0.010 inch to 0.040 inch.

Shelton discovered that a thin wax/emollient barrier in the region interjacent to the gel phase and the antiperspirant phase effectively prevents interfacial interaction. Such a wax/emollient barrier must be relatively free (i.e. present to an extent of less than about 5% by weight of the barrier phase) of particulate material (i.e. discreet solid material having a particle size of greater than about one micron). It is speculated that by providing a region of waxy material which is relatively free of the diffusion pathways provided by particulate materials, the migration of the alcohol into the antiperspirant phase is effectively prevented. Effectively isolated by the interjacent, alcohol-impermeable barrier phase, the gel phase and antiperspirant phase of the three-phase sticks exhibit negligible destructive interfacial interaction.

The barrier phase of the three phase antiperspirant stick comprises two essential components—alcohol-insoluble waxes and liquid organic emollients.

The wax or mixtures thereof are generally nonpolar compounds such as hydrocarbon waxes. Suitable waxes have a melting point within the range of from about 150° F. to 215° F., preferably within the range of from about 170° F. to 210° F. Examples of suitable waxes are ozokerite, paraffin, and ceresin.

The barrier phase contains from about 10% to 40%, preferably from about 20% to 40%, by weight of the barrier phase of the alcohol-insoluble wax. The skilled artisan will recognize that barrier phases containing higher levels of the alcohol-insoluble wax will have less desirable cosmetic characteristics. The skilled artisan may then wish to adjust the maximum thickness of barrier phases having higher wax concentrations so as to alleviate the perception of toughness.

The second essential component of the barrier phase of the three phase antiperspirant stick is a liquid organic emollient as described hereinafter in the antiperspirant phase discussion. This liquid emollient components serves to improve the cosmetic acceptability of the barrier phase herein. The emollient component comprises from about 20% to 90% by weight of the barrier phase.

The barrier phase of the preferred antiperspirant sticks described herein can contain a variety of optional ingredients suitable for improving composition stability, cosmetics or aesthetics so long as the barrier phase is relatively free of discreet particulate material and does not contain undesirable acidic materials. Such optional barrier phase components include low melting point waxes to adjust stick cosmetics, perfumes, dyes, preservatives and the like. The low-melting wax material of mixtures thereof are those having a melting point of from about 100° F. up to 150° F. Such optional waxes are referred to herein as low melting point waxes. The low melting point wax component can be used as a adjunct to the high melting point wax to provide improved emolliency and to enhance the structural integrity of the barrier phase. The low melting point wax can also be used to adjust the feel of the stick compositions. One skilled in the art will easily be able to make a product which feels more brittle, soft, slippery, sticky, rough, etc., by blending various suitable low melting point waxes with the essentially present high melting point waxes.

Examples of useful low melting point waxes include fatty acids containing from about 12 to 20 carbon atoms, fatty alcohols containing from about 12 to about 20 carbon atoms, silicone waxes and glycerol monostearate. Especially preferred materials of this type are the $C_{12}$ to $C_{20}$ fatty acids and $C_{12}$ to $C_{20}$ fatty alcohols. The most preferred low melting point waxes are cetyl alcohol, stearyl alcohol, myristyl alcohol, lauryl alcohol and glycerol monostearate.

If present, the low melting point wax component generally comprises from about 5% to 50%, and preferably from about 10% to 20% by weight of the barrier phase.

The barrier phase can also contain conventional additives such as dyes, perfumes, preservatives, deodorants, etc. If present, such materials should constitute a minor portion of the barrier phase, i.e., from about 0.1% to 1.5% by weight of the barrier phase.

Inserting Coated Pin Into Cosmetic Package or Mold Form

The coated pin described above is placed into an open end of the desired cosmetic package or mold form. The pin is then placed tightly against the opposite end which is closed by a part of the package or mold form or an entirely separate part such as a mold cap. In the preferred process of the present invention the closed end is the top of the cosmetic package, which top is closed with the cap associated with the final package.

Forming the Outer Phase

The next step in the present process is to put the molten outer phase into the space between the coated pin and the wall(s) of the cosmetic package or mold form. After the molten phase is put into the described space it is solidified by removal of heat through the package wall(s) and through the pin in which a cooling medium may be circulating. The temperature of the pin's surface should be lower than the solidification temperature of either the barrier phase or outer phase.

The preferred outer phase in the present process is either the soap gel phase or wax phase of Shelton's sticks. The most preferred outer phase is the soap gel phase.

The gel phase is formed from certain polyhydric aliphatic alcohols and certain gel-forming agents. This gel phase comprises from about 35% to 65%, preferably from about 45% to 55%, by weight of the total antiperspirant stick compositions. The primary purpose of the gel phase of the sticks is to improve the glidability and ease of application of the stick compositions onto the skin. Optionally, the gel phase can also act as a carrier for deodorant materials and for materials such as monohydric alcohols which impart a desirable cooling, moist sensation to the skin upon application.

One essential component of the gel phase of the antiperspirant stick compositions is a polyhydric aliphatic alcohol containing 2 or 3 carbon atoms and from 2 to 3 hydroxyl groups. This polyhydric alcohol or mixtures thereof is the medium which is "gelled" to form the gel phase of the stick compositions herein. The polyhydric aliphatic alcohol component of the gel phase comprises from about 10% to 92%, preferably from about 15% to 50%, by weight of the gel phase.

Suitable polyhydric alcohols for use in the gel phase include ethylene glycol, propylene glycol, trimethylene glycol, and glycerine. The most preferred polyol is propylene glycol.

The second essential component of the gel phase of the antiperspirant stick compositions is a gel forming agent which is added to the polyhydric aliphatic alcohol of the gel phase to form the desired gel material. The gel forming agents used herein can be the sodium and potassium salts (i.e. soaps) of fatty acids containing from about 14 to 18 carbon atoms.

Gel forming agents generally comprise from about 5% to 15% by weight of the gel phase, preferably from about 7% to 10% by weight of the gel phase. If the gel forming agent concentrations lower than those specified are employed, the gels formed tend to be dimensionally unstable and tend to deform at summertime temperatures. If concentrations of gel forming agents above those specified are utilized, the gels formed tend to be too hard and do not exhibit desirable glide and application characteristics. By utilizing gel-forming agents of the particular type described and in the concentrations specified, gel phases can be formulated which exhibit structural integrity and which exhibit cosmetically desirable application properties.

The fatty acid portion of the soap gel forming agents should be essentially pure saturated or unsaturated higher fatty acids having a $C_{14}$ to $C_{18}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the gel forming agents herein include myristic, palmitic, stearic, oleic, linoleic, linolenic, behenic, margaric acids and the mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids, and greases. Conventional fractionation and/or hydrolysis techniques can be employed if necessary to obtain the requisite types of fatty acids from such materials.

Preferred fatty acid soap type gel forming agents include sodium stearate, sodium palmitate, potassium stearate, potassium palmitate and sodium myristate. The most preferred gel forming agent is sodium stearate.

The gel phase of the preferred stick compositions can contain a variety of optional ingredients suitable for improving composition efficacy, stability, cosmetics and/or aesthetics. Such optional gel phase components include monohydric alcohols to improve composition cosmetics, water in small amounts, deodorant materials, alcohol evaporation retardants, and anti-syneresis agents, perfumes, dyes, pigments, coloring agents and the like.

A highly preferred optional component of the gel phase is a monohydric alcohol which serves to impart a cosmetically desirable cooling sensation to the skin. Monohydric alcohols of this type contain one to three carbon atoms. Examples of suitable monohydric alcohols include methanol, ethanol, isopropanol, and n-propanol. Preferred monohydric alcohols are ethanol and isopropanol.

While monohydric alcohols can provide a desirable cosmetic cooling benefit for the antiperspirant stick compositions herein, inclusion of a monohydric alcohol component can also lead to stick composition instability problems. Monohydric alcohols tend to produce dimensional instability of the gel phase and tend to cause the gel phase to evaporate and thereby become sticky as well as to deteriorate and assume a dried and shriveled appearance.

It has been discovered that such problems can be minimized and that monohydric alcohols can be successfully incorporated into the gel phase of the stick compositions provided certain concentration limits for the essential gel phase components are observed. When monohydric alcohols are employed, it has been found that the weight ratio of polyhydric alcohol to gel forming agent must exceed about 2.45. When polyhydric aliphatic alcohols and gel forming agents are present in this ratio, monohydric alcohols can be incorporated into the gel phase in amounts of from about 2% to 20%, preferably from about 5% to 15%, by weight of the gel phase.

When monohydric alcohols are employed, another highly preferred optional component of the gel phase is a material which helps retard alcohol evaporation and which acts as an anti-syneresis agent. Especially preferred materials of this type are cellulose derivatives such as hydroxyalkylcelluloses. Especially preferred materials of this type are hydroxypropylcellulose compounds having the chemical formula:

and wherein N is sufficiently large such that the total molecular weight of the material ranges from about 60,000 to 1,000,000. Such materials are sold under the tradename of Klucel ® by Hercules Incorporated. If present, such alcohol evaporation retarding agents and anti-syneresis agents comprise from about 0.1% to 5.0% by weight of the gel phase.

Another optional ingredient of the gel phase is a conventional deodorant material. Suitable deodorants include bacteriostatic quaternary ammonium compounds such as cetyltrimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N- hyristoyl glycine, potassium N-lauroyl sarcosine and stearyl trimethyl ammonium chloride. If present, deodorants generally comprise from about 0.1% to 1.0% by weight of the gel phase.

Conventional optional ingredients such as perfumes, dyes, pigments, coloring agents and the like can also be added to the gel phase. If present such minor additions comprise from about 0.1% to 1.5% by weight of the gel phase.

Small amounts of water can be added to the gel phase. The amount of water added should, however, be limited to less than about 10%. Water can be used as a solvent for an optional dry material or for an optional deodorant material. Water in the gel phase at concentrations exceeding 10% tends to produce a gel phase which is undesirably soft.

Removing The Pin From The Package or Mold Form

The next step in the present process is to remove the pin from the package or mold form while leaving the barrier phase attached to the outer phase. This generally involves the use of a heating medium in the pin in place of the cooling medium. The temperature of the medium is dictated by the particular type of material(s) used for the barrier and the outer phases. In one embodiment of the present invention the medium circulating within the pin is hot enough to soften but not entirely melt the barrier phase causing it to be removed from the pin and attached to the outer phase. The pin is then removed leaving a void to be occupied by the inner phase.

Filling The Space Previously Occupied By Pin

The last step in the present process is to fill in the space previously occupied by the pin and letting the inner phase material solidify. The inner phase can be formed from any of a wide variety of materials including those present in Shelton's compositions. The preferred inner phase is the antiperspirant phase of Shelton's development.

The antiperspirant phase generally serves to deliver antiperspirant material(s) to the skin via a medium which does not feel runny, cold, or sticky. The antiperspirant phase component comprises from about 35% to 65%, preferably from about 45% to 55%, by weight of the total composition. The antiperspirant phase is solid (i.e., able to retain a rigid form at 20° C.) and is shearable (i.e., yields easily when rubbed onto the skin in the normal manner of usage of cosmetic sticks.)

Many solid antiperspirant compositions are known in the art which tend to interact with soap/alcohol gels if such antiperspirant compositions are formulated into stick products along with such soap/alcohol gels. The skilled artisan can readily formulate a large number of solid compositions which have antiperspirant effectiveness and have shearable cosmetics and which are thus suitable for use as the antiperspirant phase.

In an especially preferred embodiment, the antiperspirant phase is substantially anhydrous, (i.e., comprises no more than about 1.0% by weight of the antiperspirant phase of water in addition to the waters of hydration on the antiperspirant salt), provides the antiperspirant active in an especially effective undissolved particulate form, and comprises a water-insoluble wax, a liquid organic emollient and particulate antiperspirant-active material.

A high melting point, water-insoluble wax is the principal component of the antiperspirant phase in a preferred embodiment. It is believed that the high melting point wax provides a structure which can be sheared during application to the skin, thereby depositing layers of wax and antiperspirant active particles onto the skin.

The antiperspirant phase contains from about 2% to 15%, preferably from about 3% to 11%, by weight of the antiperspirant phase of the water-insoluble wax materials. Maintenance of wax concentrations within these limits permits the realization of acceptable stick cosmetic characteristics. Furthermore, exposure to normal temperature extremes, especially during summer, might deform sticks without high melting point wax concentrations within the limits indicated.

The waxes employed as an essential component of the preferred antiperspirant phase of the sticks herein are essentially water-insoluble (soluble to an extent of less than 0.5% by weight in water at 80° F.). Such waxes have a melting point within the range of from about 150° F. to about 215° F., preferably within the range of from about 170° F. to 210° F. Such waxes are referred to as high melting point waxes. Examples of suitable high melting point waxes are beeswax, carnuba, bayberry, candelilla, montan, ozokerite, ceresin, paraffin, synthetic waxes such as Fisher-Tropsch waxes, and microcrystalline wax. Preferred high melting point waxes are ceresin, ozokerite, white beeswax and synthetic waxes. It is understood that mixtures of the high melting point waxes are also acceptable.

A second essential component of the preferred antiperspirant phase is a liquid organic emollient. The emollient component serves to improve the cosmetic acceptability by helping to impart a soft, supple character to the skin treated with the instant stick compositions.

The emollients used herein can be any non-toxic, organic material or mixtures thereof which is of low irritation potential, which is liquid at 20° C. and which is substantially water-insoluble (i.e. water solubility of from about 0.5% to 1.0% by weight in water at 20° C.). However, the liquid emollients of this invention are water-dispersible in the presence of a surfactant, e.g., soap, which is desirable in that it permits the removal of the composition during washing or bathing. The emollient component comprises from about 20% to 50%, preferably from about 30% to 40%, by weight of the antiperspirant phase.

Suitable organic emollients include fatty acid and fatty alcohol esters and water insoluble ethers. Examples of such emollients include isopropyl myristate, isopropyl palmitate, cetyl acetate, cetyl propionate, di-n-butyl phthalate, diethyl sebacate, diisopropyl adipate, ethyl carbomethyl phthalate, and the condensation product of about 14 moles of propylene oxide with one mole of butyl alcohol (Fluid AP ®). Preferred organic liquid emollients include isopropyl myristate, isopropyl palmitate, di-n-butyl phthalate, and Fluid AP ®. Especially preferred organic emollients include isopropyl myristate, isopropyl palmitate and Fluid AP ®.

Suitable emollients for use herein also include both volatile and non-volatile polyorganosiloxane materials. Suitable volatile silicones are described in U.S. Pat. No. 4,265,878, May 5, 1981 to Keil, incorporated herein by reference.

The antiperspirant phase of the preferred sticks made using the present process additionally contains from about 15% to about 60% by weight of the antiperspirant phase of a particulate astringent antiperspirant material. Such materials are generally zirconium and/or aluminum salts and are described in detail in the Shelton patent incorporated in total herein by reference.

The following example illustrates a preferred embodiment of this invention.

EXAMPLE

The composition disclosed by Shelton and discussed hereinabove are the preferred compositions for use with the process of the present invention.

The preferred barrier phase comprises from about 20% to about 40% of an alcohol insoluble wax and from about 20% to about 90% of an emollient. Preferably the wax is ozokorite wax and the emollient is Fluid AP ®. The wax/emollient mixture is heated to a temperature of from about 230° F. to 240° F. and kept at that temperature.

A hollow cylindrical pin closed at one end and having 80° F. water circulating in a closed line within the pin is prepared for coating. At a point just before the pin is inserted into the barrier bath, open end first, it contacts a plug which fits into the pin's open end. The plug has a gasket attached to it to make the connections secure. As the pin is pushed down further, it causes the plug to be depressed due to a spring attached to the plug. Once the pin is fully submerged in the barrier bath, it is left in the bath for a minimum of about 0.5–1.5 seconds and withdrawn. As the pin is withdrawn, a barrier film of about 0.017" thick is left on the surface of the pin. The pin is made of polished, anodized stainless steel of aluminum.

The coated pin is then seated into the antiperspirant package from the open bottom end, the seating being against the top of the package closed by the package's cap.

The gel phase, comprising a mixture of Fluid AP ®, propylene glycol, ethanol and sodium stearate is heated to a temperature of from about 170° F. to about 220° F., preferably about 180° F. and kept there until all of the gel phase components are melted. Other gel components such as dyes, perfumes and a deodorant active are added at this time. The gel is then cooled to a temperature of about 130° F. before it is put into the package, between the parrier coated pin and the package wall.

The water circulating within the pin is increased in temperature to about 160° F. This temperature melts some of the barrier allowing the barrier to be removed from the pin while the barrier still adheres to the solidified gel phase. The pin is removed carefully leaving the barrier intact.

Finally the wax inner phase is prepared containing a particulate antiperspirant active, a high melting point wax such as ozokerite wax, an emollient such as Fluid AP ® and other minor ingredients and is heated to 170° F. to 210° F. and kept there until all of the wax components have melted. The wax antiperspirant phase is then cooled to about 160° F. and filled into the space previously occupied by the pin.

The finished stick is then attached to an elevator platform by gluing the two together with melted barrier phase.

What is claimed is:

1. A process for preparing a product containing two incompatible phases separated by a thin film barrier phase comprising:
   A. dipping a pin of appropriate size and possessing heat transferring capability into a molten bath of the barrier phase material, said pin's outer surface having a temperature below the solidification temperature of said barrier phase.
   B. withdrawing said pin from said barrier bath with a solidified film of said barrier material left on its surface;
   C. placing the coated pin into an open end of a container designed to contain the product, the coated pin being placed tightly against an opposite end of said container which is closed;
   D. putting a molten outer phase material into a space between said coated pin and the outer wall(s) of said container, maintaining the temperature of the outer surface of said coated pin below the solidification temperatures of the barrier phase and the outer phase materials thereby allowing the outer phase material to solidify;
   E. increasing the temperature of said pin sufficiently to allow barrier phase material to attach to said solidified outer phase and removing said pin from said container; and;
   F. pouring molten inner phase material into the space previously occupied by said pin and allowing said inner phase material to solidify.

2. A process according to claim 1 wherein the product is a cosmetic stick.

3. A process according to claim 2 wherein the inner phase is either a soap gel or a wax solid.

4. A process according to claim 3 wherein the inner phase is a wax solid and the outer phase is a soap gel.

5. A process according to claim 4 wherein the inner phase material contains an antiperspirant active.

6. A process according to claim 5 wherein the product is formed in the final package.

7. A process according to claim 1 wherein the pin has cooling water circulating therein during the barrier forming step.

8. A process according to claim 7 wherein hot water is circulating within the pin during the barrier release and attachment to the outer phase step.

9. A process according to claim 8 including forming the product in the final package, the filling being from the bottom and the package top being closed by a package cap.

10. A process according to claim 6 wherein the barrier phase is a waxy solid.

* * * * *